United States Patent [19]

Sakakibara

[11] Patent Number: 5,958,393
[45] Date of Patent: *Sep. 28, 1999

[54] PERMANENT-WAVE TREATMENT METHOD AND A PERMANENT-WAVE TREATMENT AUXILIARY AGENT

[75] Inventor: Yasuyuki Sakakibara, Nagoya, Japan

[73] Assignee: Itsuo Sakakibara, Los Angeles, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/811,656

[22] Filed: Mar. 5, 1997

[30] Foreign Application Priority Data

May 13, 1996 [JP] Japan ..................................... 8-117543

[51] Int. Cl.$^6$ ....................................................... A61K 7/06
[52] U.S. Cl. ........................ 424/70.2; 424/70.4; 424/70.5; 424/70.51; 424/62; 132/204; 132/205
[58] Field of Search ................................. 424/70.2, 70.4, 424/70.5, 70.51, 62; 132/204–205

[56] References Cited

U.S. PATENT DOCUMENTS

| | | | |
|---|---|---|---|
| 3,726,967 | 4/1973 | Vorsatz | 424/62 |
| 5,101,841 | 4/1992 | Crews | 132/203 |
| 5,294,436 | 3/1994 | Cope | 424/62 |
| 5,575,989 | 11/1996 | Caskey | 424/62 |

FOREIGN PATENT DOCUMENTS

| | | | |
|---|---|---|---|
| 59-162035 | 7/1986 | Japan | A61K 7/09 |
| 63-207564 | 5/1990 | Japan | A61K 7/06 |
| 7-158332 | 12/1996 | Japan | A45D 44/12 |

*Primary Examiner*—D. Gabrielle Brouillette
*Attorney, Agent, or Firm*—Joseph C. Mason, Jr.; Dennis G. LaPointe; Mason & Assoc., P.A.

[57] ABSTRACT

A permanent-wave treatment method which can give a permanent-wave comfortably without using a cap or a turban, and a treatment auxiliary agent used in this method. The permanent-wave treatment method comprises a winding step of applying permanent-wave treatment liquid to hair and winding the hair around rollers, and a liquid drop prevention step of sprinkling a powdery treatment auxiliary agent on the wound hair so as to prevent the permanent-wave treatment liquid from dropping. The treatment auxiliary agent comprises powder which adsorbs or partially dissolves in permanent-wave treatment liquid, and serves to increase the viscosity of the powder-sprinkled permanent-wave treatment liquid and prevent the permanent-wave treatment liquid from dropping.

3 Claims, No Drawings

PERMANENT-WAVE TREATMENT METHOD AND A PERMANENT-WAVE TREATMENT AUXILIARY AGENT

BACKGROUND OF THE INVENTION

1. Field of the Invention

The present invention relates to a permanent-wave treatment method and a permanent-wave treatment auxiliary agent used in this method.

2. Description of the Prior Art

A permanent-wave treatment method is to apply permanent-wave treatment liquid to hair for the purpose of removing elasticity from the hair and giving flexibility to the hair by the reduction force of the permanent-wave treatment liquid, to wind the hair in certain curls, and then to oxidize the hair reversely for the purpose of restoring the elasticity of the hair and setting curls. During this permanent-wave treatment, there arises a problem: The permanent-wave treatment liquid drops on and contacts skin.

Conventionally, measures such as covering a head with a cap and winding a head with a towel like a turban have been taken in order to protect skin from drops of permanent-wave treatment liquid.

When a head is covered with a cap or wound with a towel like a turban, however, there arise problems: The cap sometimes drops, and rollers sometimes fall off from hair due to the turban. In addition, permanent-wave treatment liquid often drops from the edge of the cap or turban.

SUMMARY OF THE INVENTION

The present invention has been conceived to dissolve these problems.

It is an object of the present invention to provide a permanent-wave treatment method which can give a permanent-wave comfortably without using a cap or a turban.

It is another object of the present invention to provide a permanent-wave treatment auxiliary agent used in this method.

The present inventor, has conceived sprinkling of a powdery permanent-wave treatment auxiliary agent on wound hair on rollers so as to increase the power of holding permanent-wave treatment liquid and prevent the permanent-wave treatment liquid from dropping. The inventor has confirmed through various experiments that this achieves the prevention of permanent-wave treatment liquid drop, and has completed the present invention.

The permanent-wave treatment method according to the present invention comprises a winding step of applying permanent-wave treatment liquid to hair and winding the hair around rollers, and a liquid drop prevention step of sprinkling, on the wound hair, a permanent-wave treatment auxiliary agent comprising powder so as to prevent the permanent-wave treatment liquid from dropping.

The permanent-wave treatment auxiliary agent according to the present invention comprises powder which adsorbs or partially dissolves in permanent-wave treatment liquid. This treatment auxiliary agent adsorbs or dissolves in dropping permanent-wave treatment liquid, so as to increase the powder of holding the dropping permanent-wave treatment liquid and hold the permanent-wave treatment liquid on the surface of wound hair.

The permanent-wave treatment method according to the present invention achieves the prevention of permanent-wave treatment liquid drop only by sprinkling a powdery treatment auxiliary agent on the surface of hair wound around rollers. Therefore, the operation is very simple, and people who have their hair permed needn't bear uncomfortable acts such as wearing a cap or a turban. That is to say, they can have their hair permed comfortably.

It must be noted that the term "permanent-wave" used in this invention means not only the permanent rendering of a wavy or curly shape to hair but also the permanent rendering of a straight shape to hair. Therefore, the present inventive method and the present inventive auxiliary agent can be used in straightening wavy or curly hair permanently.

DETAILED DESCRIPTION OF THE PRESENT INVENTION

The permanent-wave treatment method according to the present invention comprises a winding step and a liquid drop prevention step. The winding step is a step of applying permanent-wave treatment liquid to hair and winding the hair around rollers. The winding step is the same step as used in the conventional permanent-wave treatment method. The permanent-wave treatment method according to the present invention is characterized in the liquid drop prevention step, and constituted by adding a liquid drop prevention step to the conventional permanent-wave treatment method.

First, the winding step according to the present invention will be described.

A permanent-wave treatment method comprises applying permanent-wave treatment liquid to hair so as to remove elasticity from the hair and give flexibility to the hair by the reduction force, winding the hair in certain curls, and then oxidizing the hair so as to restore elasticity of the hair and set curls into the hair permanently. Generally known permanent-wave treatment liquids are classified as single bath treatment liquid, two bath treatment liquid, and three bath treatment liquid. The single bath permanent-wave treatment liquid only comprises a reduction agent, and oxygen in the atmosphere is used as an oxidation agent. The two bath permanent-wave treatment liquid comprises a first treatment liquid composed mainly of a reduction agent, and a second treatment liquid composed mainly of an oxidation agent. The three bath treatment liquid comprises two bath permanent-wave treatment liquid and a winding lotion composed mainly of a hair moisturizing and softening agent.

As a reduction agent, two types of agents can be employed: one composed mainly of thioglycololate, and one composed mainly of cysteine. Some reduction agents include both thioglycolate and cysteine. When a reduction agent is applied to and contacted with hair, nascent hydrogen generates and this nascent hydrogen cuts a side chain of cystine linkage in the hair. Accordingly, the elasticity of the hair gets lost, and flexibility is rendered to the hair.

An oxidation agent exerts a action reverse to a reduction agent, and serves to oxidize and connect the broken cystine linkage in the hair. Thus, the hair loses flexibility and restores the original elasticity. Examples of suitable oxidation agents include bromate such as sodium bromate, peroxoborate such as sodium peroxoborate, hydrogen peroxide, oxygen in the air, and the like.

The winding step makes use of the action of a reduction agent, and is to apply a reduction agent to hair so as to remove elasticity from the hair and give flexibility to the hair. The hair in this state is wound around rollers. Flexible hair easily deforms in conformity with the outer peripheral shape of the rollers, whereby curls are rendered to the hair.

The hair wound around the rollers is contacted with an oxidization agent. The cystine linkage reduced by the action of the oxidation agent is oxidized, and the side chain of the cystine linkage is closed again. Thus, the hair loses flexibility and restores elasticity, thereby setting the curls into the hair permanently. That is to say, a permanent-wave is given to the hair.

The winding step according to the present invention includes applying at least a reduction agent to hair and winding the hair around rollers. In the case of using two or three bath treatment liquid, the operations of applying a winding lotion, a reduction agent and an oxidation agent to hair can be recognized as part of the winding step.

A treatment auxiliary agent used in the liquid drop prevention step comprises powder which adsorbs or partially dissolves in permanent-wave treatment liquid. This powder is sprinkled on the permanent-wave treatment liquid to increase the viscosity of the permanent-wave treatment liquid. Thus, the permanent-wave treatment liquid is prevented from dropping. To be concrete, it is preferable that this treatment auxiliary agent is hydrophilic organic powder or hydrophilic inorganic powder.

"Hydrophilic" means to possess the property of being easily wet with water. Hydrophilic organic powder is organic materials having such hydrophilic group as hydroxyl group, carboxyl group, and ester group. For example, saccharide, alcohol, carboxylic acid, and ester can be used as hydrophilic organic powder. These organic materials must have a solid state at room temperature. As hydrophilic inorganic powder, oxides of various metals can be employed. To be concrete, it is preferable to employ inorganic materials having large specific surface areas such as clay minerals, silica, and alumina.

In the liquid drop prevention step, when one bath permanent-wave treatment liquid is used, the permanent-wave treatment liquid is sufficiently applied to hair, and the hair is wound around rollers, and then this powdery treatment auxiliary agent is sprinkled on the outer side of the wound hair. The treatment auxiliary agent serves to increase the viscosity of excessive permanent-wave treatment liquid which oozes from the wound hair, so as to increase the hair power of holding the permanent-wave treatment liquid. The treatment auxiliary agent does not serve to draw the permanent-wave treatment liquid from the hair. Accordingly, it is not desirable to use a large amount of the treatment auxiliary agent. Owing to this, the permanent-wave treatment liquid acting on hair is sufficiently held on the hair and the liquid can be prevented from dropping. In the case of using single bath permanent-wave treatment liquid, as time passes, a reduction agent contained in the permanent-wave treatment liquid disappears and oxidation proceeds by using oxygen in the air so as to restore the elasticity of hair and set the wavy or curly shape into the hair permanently.

In the case of using two bath treatment liquid, first a reduction agent is applied to hair, and then the hair is wound around rollers. A liquid drop prevention step can be carried out in this stage. Time for the reduction agent to act on the hair is relatively short, and it requires some time to wind hair around rollers. A beauty specialist always keeps an eye on the hair during the winding operation, so the beauty specialist can promptly take care of liquid drop, if there is any. Therefore, it is not necessary to take a liquid drop prevention step in this stage.

In the case of using two bath treatment liquid, after the hair is wound around rollers, exhibits sufficient flexibility, and attains a wavy or curly shape, an oxidation agent is applied to the hair. The oxidation agent permeates and oxidizes the hair, and as a result, restores the elasticity of the hair. In order to prevent the liquid drop of the oxidation agent, a treatment auxiliary agent is sprinkled on the surface of the hair. Thus, liquid is prevented from dropping.

On the other hand, it is possible to sprinkle a treatment auxiliary agent on the surface of hair and form a thin film of the treatment auxiliary agent before an oxidation agent is applied to the hair. In this case, the oxidation agent permeates the hair through this film of the treatment auxiliary agent.

Some kinds of permanent-wave treatment liquid require rinsing-out of a reduction agent before an oxidation agent is applied.

After the hair completely restores elasticity and has the curls set into the hair permanently owing to the action of the oxidation agent, the hair is rinsed with water, thereby rinsing away the permanent-wave treatment liquid. Thus, a desired permanent-wave is given to the hair.

In operation, in the permanent-wave treatment method according to the present invention, after permanent-wave treatment liquid is applied to hair and the hair is wound around rollers, a treatment auxiliary agent is sprinkled on the wound hair. Since the treatment auxiliary agent is hydrophilic, the treatment auxiliary agent is wet with the permanent-wave treatment liquid, adsorbs excessive permanent-wave treatment liquid or partially dissolves in permanent-wave treatment liquid so as to increase the viscosity of the permanent-wave treatment liquid. So, a high-viscous film of permanent-wave treatment liquid is formed on the surface of the hair wound around the rollers. Thus, the permanent-wave treatment liquid is prevented from dropping.

Advantages of the present invention are as follows.

The sprinkling of a powdery treatment auxiliary agent on wound hair prevents permanent-wave treatment liquid from dropping. In this permanent-wave treatment method, there is no need to wear a cap or wind a towel around the head in order to prevent permanent-wave treatment liquid from dropping. Therefore, perming operations become simpler, and people can have their hair permed comfortably without being troubled with wearing of a cap or the like.

PREFERRED EMBODIMENT OF THE PRESENT INVENTION

For the application of a permanent-wave to hair, first a diagnosis of hair is given and the type of reduction agent is determined. Second, the hair is shampooed, dried, and if necessary, cut. Further, the type of permanent-wave treatment liquid, for example, whether the hard type or the soft type is used is determined in accordance with results of the hair diagnosis and counseling of a person who will have the hair permed.

A perm solution including the determined type of reduction agent is applied to hair. At this time, caution must be exercised in order that the perm solution does not contact the scalp. Then the hair is wound around rollers. The hair loses elasticity, attains flexibility, and has curls set into the hair in about ten to fifteen minutes. After it is confirmed that the hair attains curls firmly, the hair is soaked with a perm solution including an oxidation agent. Then, a treatment auxiliary agent is sprinkled so as to increase the viscosity of excessive perm solution and prevent the perm solution from dropping.

Powder of sodium calboxymethylcellulose known as CMC (sodium cellulose glycolate) is used in this preferred embodiment. This treatment auxiliary agent is sprinkled on the hair wound around rollers to make a thin film. Since the perm solution is fixed by this film of the treatment auxiliary agent, the perm solution does not drop. The hair is kept in this state for five to fifteen minutes, and after the hair is oxidized to restore elasticity and has the curls firmly set into the hair, the hair is rinsed with water to rinse away the perm solution containing the treatment auxiliary agent, and then subjected to finishing. Thus, a permanent-wave is given to the hair.

In this preferred embodiment, the treatment auxiliary agent is sprinkled after the hair is soaked with the perm solution containing the oxidation agent. However, it is possible to sprinkle a treatment auxiliary agent on hair prior to the soaking of hair with a perm solution including an oxidation agent, and form a thin film of the treatment auxiliary agent, and make a perm solution containing an oxidation agent permeate the hair. In this case, perm solution enough to oxidize hair can permeate hair easily without dropping.

Obviously, many modifications and variations of the present invention are possible in the light of the above teachings. It is therefore to be understood that within the scope of the appended claims, the invention may be practiced otherwise than as specifically described.

What is claimed is:

1. A method of preventing the dropping of the liquid agents of a permanent waving treatment of hair comprising, in sequence, the steps of:
   (1) applying a first liquid agent comprising a reducing agent to the hair for a period of time sufficient to reduce the hair;
   (2) winding the hair onto hair rollers;
   (3) applying a second liquid agent comprising an oxidizing agent to the hair for a period of time sufficient to oxidize the hair;
   (4) rinsing the hair with water; and
   (5) the additional step of applying an auxiliary agent comprising hydrophilic organic powder having as a hydrophilic group a hydroxyl, carboxyl or ester directly to the hair as a dry powder either before or after step 3 but before step 4 above, and leaving the auxiliary agent upon the hair for a period of 5 to 15 minutes sufficient to absorb any excessive liquid agent.

2. Method according to claim 1 wherein the auxiliary agent is selected from the group consisting of saccharine, alcohol, carboxylic acid and ester.

3. A method of preventing the dropping of the liquid agents of a permanent waving treatment of hair comprising, in sequence, the steps of:
   (1) applying a first liquid agent comprising a reducing agent to the hair for a period of time sufficient to reduce the hair;
   (2) winding the hair onto hair rollers;
   (3) applying a second liquid agent comprising an oxidizing agent to the hair for a period of time sufficient to oxidize the hair;
   (4) rinsing the hair with water; and
   (5) the additional step of applying an auxiliary agent comprising sodium cellulose glycolate directly to the hair as a dry powder either before or after step 3 but before step 4 above, and leaving the auxiliary agent upon the hair for a period of 5 to 15 minutes sufficient to absorb any excessive liquid agent.

* * * * *